US00PP21271P2

(12) United States Plant Patent
Meilland

(10) Patent No.: US PP21,271 P2
(45) Date of Patent: Sep. 7, 2010

(54) FLORIBUNDA ROSE PLANT NAMED 'MEIKOKAN'

(50) Latin Name: *Rosa hybrida*
Varietal Denomination: Meikokan

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 12/585,551

(22) Filed: Sep. 17, 2009

(51) Int. Cl.
*A01H 5/00* (2006.01)

(52) U.S. Cl. ..... Plt./145

(58) Field of Classification Search ..... Plt./145
See application file for complete search history.

*Primary Examiner*—Annette H Para
(74) *Attorney, Agent, or Firm*—Buchanan Ingersoll & Rooney PC

(57) ABSTRACT

A new and distinct Floribunda rose plant is provided which forms in abundance on a substantially continuous basis attractive orange-colored blossoms. The blossoming commonly commences early in the season. The plant exhibits strong vegetation, a bushy growth habit, and dark green foliage with a semi-glossy aspect. No particular disease concern has been encountered during observations to date. The attractive dark green foliage contrasts nicely with the orange blossom coloration. The new variety is well suited for growing as attractive ornamentation in parks and gardens.

1 Drawing Sheet

Botanical/commercial classification: *Rosa hybrida*/Floribunda Rose Plant.
Varietal denomination: cv. Meikokan.

SUMMARY OF THE INVENTION

The new variety of *Rosa hybrida* Floribunda rose plant was created by artificial pollination wherein two parents were crossed which previously had been studied in the hope that they would contribute the desired characteristics. The female parent (i.e., the seed parent) was the 'Macivy' variety (U.S. Plant Pat. No. 8,362). The male parent (i.e., the pollen parent) was the product of the cross of the 'Meigekanu' variety (U.S. Plant Pat. No. 6,384) and the 'Delge' variety (non-patented in the United States. The parentage of the new variety can be summarized as follows:

'Macivy'×('Meigekanu'×'Delge').

The seeds resulting from the above pollination were sown and small plants were obtained which were physically and biologically different from each other. Selective study resulted in the identification of a single plant of the new variety.

It was found that the new Floribunda rose plant of the present invention:

(a) exhibits a bushy growth habit with strong vegetation,
(b) forms in abundance on a substantially continuous basis attractive orange-colored blossoms,
(c) forms attractive dark green semi-glossy foliage,
(d) displays good tolerance to disease, and
(e) is well suited for growing as ornamentation in parks and gardens.

No particular disease concern has been encountered during observations to date. Blossoming tends to commence early in the season. The dark green foliage coloration contrasts nicely with the orange blossom coloration.

The new variety well meets the needs of the horticultural industry and can be grown to advantage outdoors where attractive ornamentation is desired.

The new variety can be readily distinguished from its ancestors. For instance, 'Macivy' displays a dissimilar upright growth habit and forms multi-colored blossoms having apricot and red tones. The 'Meigekanu' variety forms bright red blossoms, and the 'Delge' variety forms soft rose-colored blossoms.

The new variety has been found to undergo asexual propagation in France by a number of routes, including budding, grafting, and the use of cuttings. Asexual propagation by the above-mentioned techniques in France has shown that the characteristics of the new variety are stable and are strictly transmissible by such asexual propagation from one generation to another. Accordingly, the new variety undergoes asexual propagation in a true-to-type manner.

The new variety has been named 'Meikokan'.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately one year of age and were observed during July while budded on Rosa laxa understock and growing outdoors at Le Cannet des Maures, Var, France. Dimensions in centimeters are indicated at the bottom of the photograph together with comparative color information.

FIG. 1 — illustrates a specimen of a young shoot;

FIG. 2 — illustrates a specimen of a floral bud before the opening of the sepals;

FIG. 3 — illustrates a specimen of a floral bud at the opening of the sepals;

FIG. 4 — illustrates a specimen of a floral bud at the opening of the petals;

FIG. 5 — illustrates a specimen of a flower in the course of opening;

FIG. 6 — illustrates a specimen of an open flower — plan view — obverse;

FIG. 7 — illustrates a specimen of an open flower — plan view — reverse;

FIG. 8 — illustrates a specimen of a fully open flower — plan view — obverse;

FIG. 9 — illustrates a specimen of a fully open flower — plan view — reverse;

FIG. 10 — illustrates a specimen of a floral receptacle showing the arrangement of the stamens and pistils;

FIG. 11 — illustrates a specimen of a floral receptacle showing the arrangement of the pistils (stamens removed);

FIG. 12 — illustrates a specimen of a flowering stem;

FIG. 13 — illustrates a specimen of a main branch;

FIG. 14 — illustrates a specimen of a leaf with three leaflets — plan view — upper surface (left), and under surface (right); and FIG. 15 — illustrates a specimen of a leaf with five leaflets — plan view — upper surface (left), and under surface (right).

DETAILED DESCRIPTION

The chart used in the identification of the colors is that of The Royal Horticultural Society (R.H.S. Colour Chart), London, England. Common color terms are to be accorded their customary dictionary significance. The description is based on the observation of two-year-old plants during October while budded on Rosa laxa understock and growing outdoors at Le Cannet des Maures, Var, France.

Class: Floribunda.

Plant:

*Habit.*—Bushy.

Branches:

*Color.*—Young stems: near Green Group 143B. Adult wood: near Green Group 138A.

*Thorns.*—On young stems: Small prickles: commonly absent. Long prickles: Configuration: Upright, rather elongated on the upper surface, slightly concave on the under surface, and with an upright and long base. Quantity: Approximately 4 on average on a stem length of 10 cm. Length: Approximately 9 mm on average. Color: Near Yellow-Green Group 148B. on adult stems: Small prickles: Commonly absent. Long prickles: Configuration: Upright, rather elongated on the upper surface, slightly concave on the under surface, and with an upright and long base. Quantity: Approximately 10 on average on a stem length of 18 cm. Length: Approximately 9 mm on average. Color: Near Greyed-Orange Group 177B.

Leaves:

*Stipules.*—Adnate, pectinate, and narrow, approximately 1.7 cm in length on average, approximately 5 mm in width on average, near Yellow-Green Group 145A on the upper surface, and near Yellow-Green Group 144B on the under surface.

*Petioles.*—Upper surface: Near Yellow-Green Group 146D in coloration. Under surface: Near Yellow-Green Group 144A in coloration. Texture: Smooth, non-glandular, and commonly without prickles. Length: Approximately 2.7 cm for the terminal leaflet.

*Rachis.*—Upper surface: Near Yellow-Green Group 146B in coloration. Undersurface: Near Green Group 146D in coloration. Texture: Smooth.

*Leaflets.*—Number: 3, and most often 5 and 7. Shape: Generally oval with an obtuse base and an acuminate tip. Size: The terminal leaflets commonly are approximately 6.6 cm in length on average, and approximately 3.9 cm in width on average. Serration: Small and single (as illustrated). Texture: Smooth, physically firm and thick. General appearance: Very dense with a semi-glossy aspect on the upper surface. Color (young foliage): Upper surface: Near Green Group 141B. Under surface: Near Green Group 137D. Color (adult foliage): Upper surface: Near Green Group 139A. Under surface: near Green Group 138A.

Inflorescence:

*Number of flowers.*—Commonly 1 to 4 per stem.

*Peduncle.*—Pubescent, near Yellow-Green Group 144B in coloration, approximately 5 to 6 cm in length on average, and approximately 0.3 cm in diameter on average.

*Sepals.*—Upper surface: Tomentose and near Green Group 138B in coloration. Under surface: Smooth and near Green Group 143B in coloration. Configuration: Longish, relatively narrow, upright at the base, approximately 2.8 cm in length on average, and approximately 1 cm in width on average at the widest point.

*Buds.*—Shape: Conical. Size: Medium. Length: Approximately 1.5 cm on average. Width: Approximately 1 cm on average at the widest point. Color: Upper surface: Near Orange Group 25B suffused with near Red Group 37B as the calyx breaks. Under surface: Near Orange-Red Group 34B as the calyx breaks.

*Flower.*—shape: Cup-shaped. Diameter: Approximately 7 to 8 cm on average when fully open. Color (in the course of opening): Upper surface: Near Orange Group 25B suffused with near Red Group 37B. Under surface: Orange-Red Group 34B. Basal petal spot: Near Yellow-Orange Group 17C. Color (when fully open): Upper surface: Near Red Group 37D. Under surface: Near Red Group 52C. Basal petal spot: Near Yellow-Orange Group 17C. Fragrance: Very slight. Petal number: Commonly approximately 25 to 27 on average under normal growing conditions. Petal shape: Rounded base and a cuneiform tip. Petal length: Commonly approximately 3.2 cm on average. Petal width: Commonly approximately 2.7 cm on average. Petal texture: somewhat leathery. Petal arrangement: Imbricated, and without petaloids. Petal drop: Good with the petals commonly detaching cleanly before drying. Stamen number: Approximately 162 on average. Anthers: Regularly arranged around the styles, approximately 3 mm in size on average, and near Yellow-Orange Group 17B in coloration. Pollen: Present. Filaments: Approximately 7 mm in length on average, and near Yellow Group 3C in coloration. Pistils: Approximately 78 on average. Stigmas: Approximately 1 mm in size on average, and near Yellow-Green Group 150D in coloration. Styles: Approximately 8 mm in length on average, and near Yellow-Green Group 150D in coloration. Receptacle: Smooth, pitcher-shaped in longitudinal section, approximately 8 mm in length on average, approximately 1.2 cm in width on average at the widest point, and near Green Group 143B in coloration.

Development:

*Vegetation.*—Strong.

*Blooming.*—Early, very abundant, and substantially continuous.

*Resistance to diseases.*—Very good, with no particular disease concern having been encountered during observations to date.

I claim:

1. A new and distinct Floribunda rose plant characterized by the following combination of characteristics:

(a) exhibits a compact bushy growth habit with strong vegetation, (b) forms in abundance on a substantially continuous basis attractive orange-colored blossoms, (c) forms attractive dark green semi-glossy foliage, (d) displays good tolerance to disease, and (e) is well suited for growing as ornamentation in parks and gardens; substantially as herein shown and described.

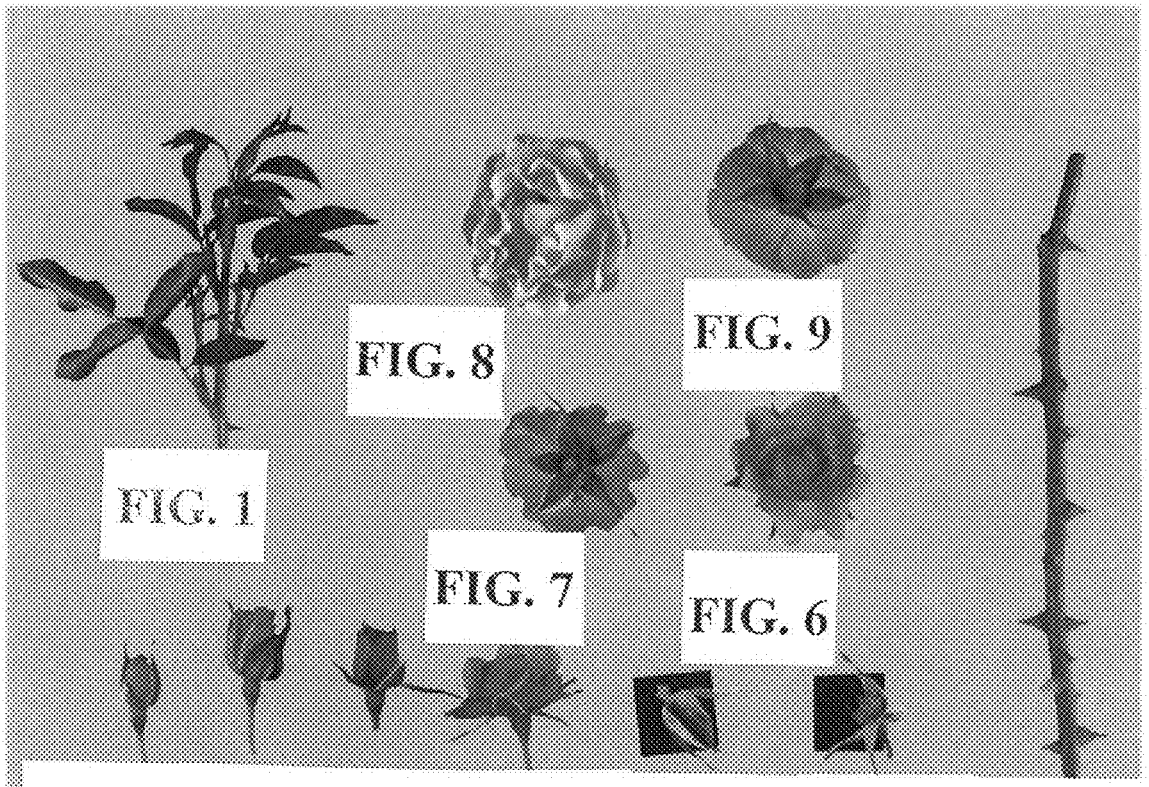
FIG. 2 FIG. 3 FIG. 4 FIG. 5 FIG. 11 FIG. 10 FIG. 13
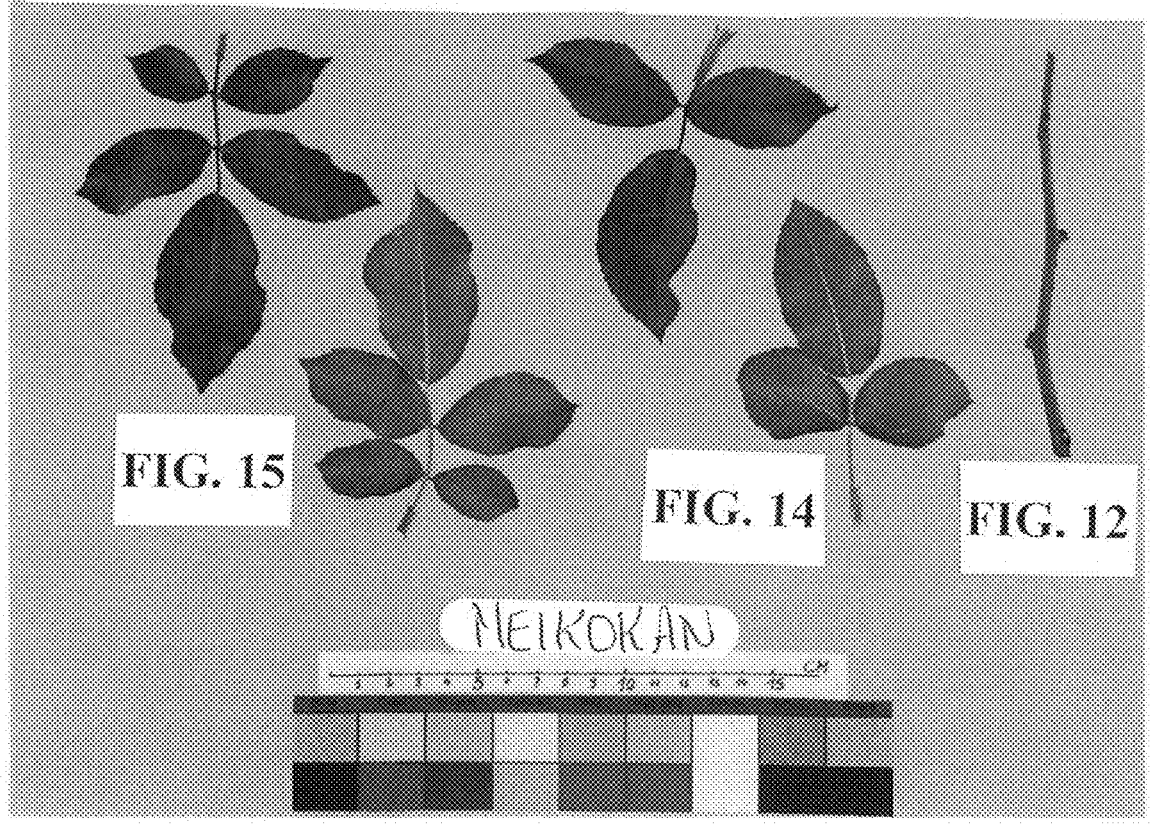

* * * * *